(12) United States Patent
Pruss et al.

(10) Patent No.: US 7,572,058 B2
(45) Date of Patent: Aug. 11, 2009

(54) PATIENT POSITIONING DEVICE OF A PANORAMIC DENTAL X-RAY APPARATUS

(75) Inventors: Malte Pruss, Alsbach-Hähnlein (DE); Michael Döbert, Lorsch (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 11/905,257

(22) Filed: Sep. 28, 2007

(65) Prior Publication Data

US 2008/0081312 A1    Apr. 3, 2008

(30) Foreign Application Priority Data

Sep. 28, 2006    (DE) ................ 10 2006 046 271

(51) Int. Cl.
*H05G 1/00*    (2006.01)
(52) U.S. Cl. ..................................... 378/208
(58) Field of Classification Search ............. 378/38–40, 378/204, 205, 64, 68, 167, 177, 180, 208
See application file for complete search history.

(56) References Cited

U.S. PATENT DOCUMENTS

| | | | | |
|---|---|---|---|---|
| 4,782,503 A | | 11/1988 | Molitor et al. | 378/169 |
| 2006/0056582 A1 | | 3/2006 | Stoeckl | 378/38 |
| 2006/0227939 A1* | | 10/2006 | Walker et al. | 378/208 |

FOREIGN PATENT DOCUMENTS

| | | |
|---|---|---|
| DE | 3609260 | 9/1987 |
| DE | 102004041440 | 3/2006 |
| WO | 02/086619 | 10/2002 |
| WO | 2006/024342 | 3/2006 |

* cited by examiner

*Primary Examiner*—Courtney Thomas
(74) *Attorney, Agent, or Firm*—Dykema Gossett PLLC

(57) ABSTRACT

A positioning device for positioning a patient when being radiographed with a panorama X-ray machine 10 includes a retainer 18 disposed in a fixed direction relative to the X-ray apparatus 10 and a variable positioner connected thereto, for example a bite block 19 or a support, the retainer including a longitudinal guide 20 for guiding the positioner 19 such that the positioner 19 is guided in the retainer 18 for vertical adjustment in a longitudinal direction.

6 Claims, 1 Drawing Sheet

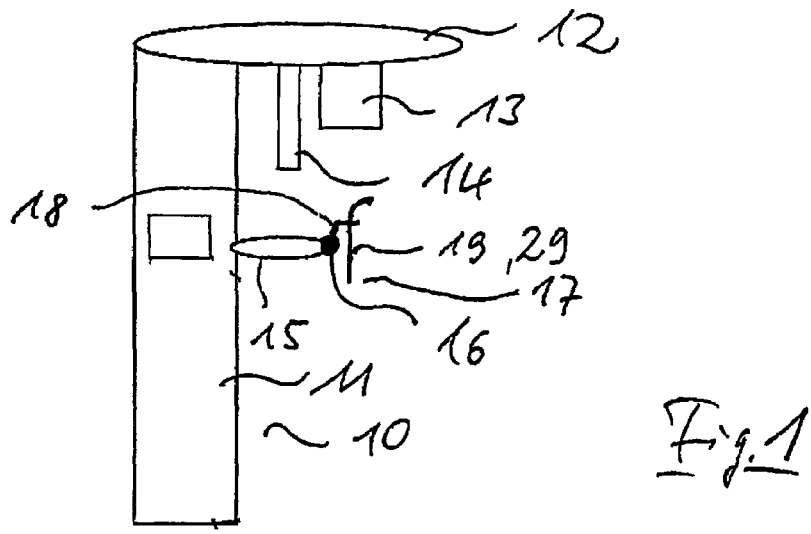
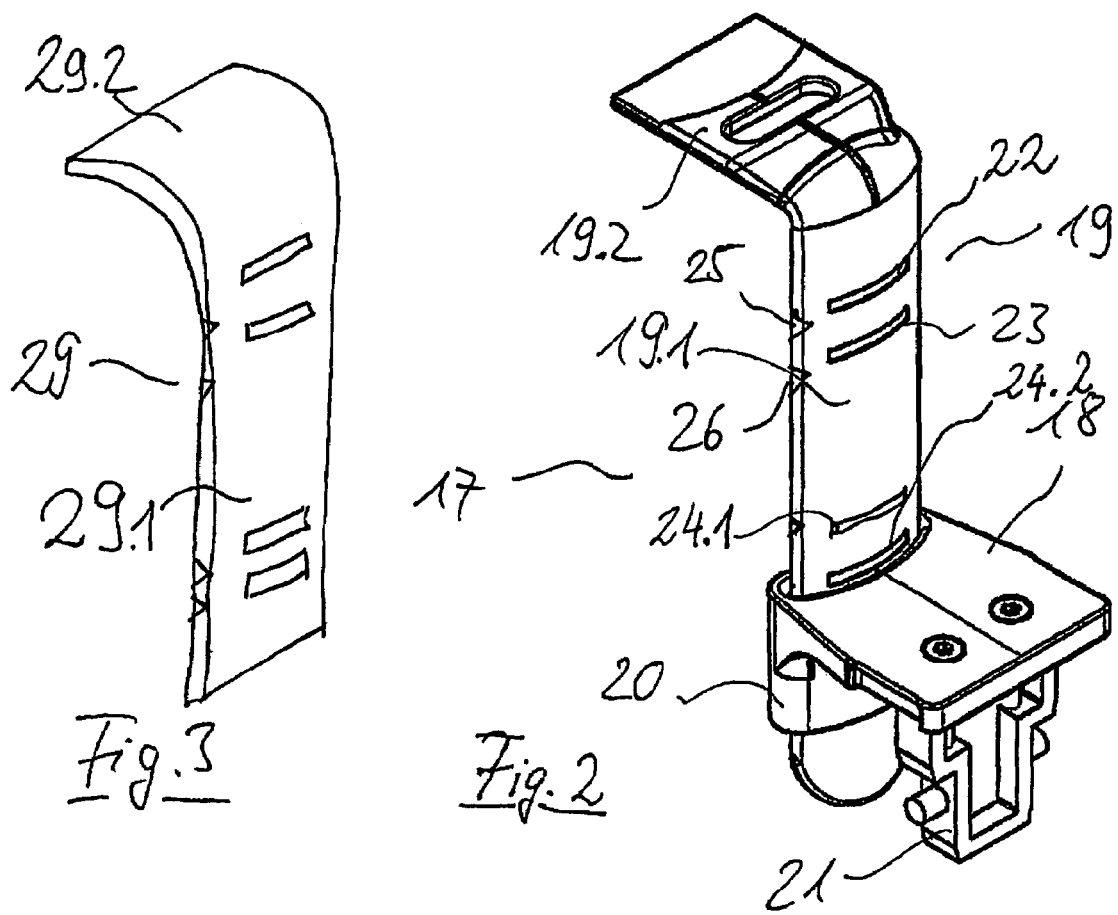

PATIENT POSITIONING DEVICE OF A PANORAMIC DENTAL X-RAY APPARATUS

TECHNICAL FIELD

The invention relates to a positioning device for correct positioning of a patient when being radiographed with a panorama X-ray imaging device.

PRIOR ART

When a panorama X-ray camera is used, the operator must position the patient prior to take the radiograph and optionally also during the radiographing procedure. This is accomplished with a positioning device comprises a bite block or a positioning support. For different types of radiographs, the positioner must be interchanged in order to permit positioning at different levels. As a result of the change, despite all precautionary measures, the situation may arise that a bite block unsuitable for radiographing is used. Furthermore, for patients having no front teeth, other positioning supports may be necessary, such as a subnasal positioning support that the patient does not bite on but rather against which he rests.

DE 36 09 260 A1 discloses a panorama X-ray device for producing panorama X-ray radiographs and having three exchangeable bite blocks. A first bite block is provided for so-called standard radiographs, a second bite block for so-called sinus and mandibular radiographs. A third bite block is also suitable for mandibular radiographs but for an X-ray beam coming from a different direction. The bite blocks have sockets which are of the same design so that one or other of the bite blocks can be inserted into a retaining guide shaft of a support member. In order to distinguish the bite blocks from each other, they have different identification marks, particularly in the form of color-code marks.

DE 35 30 234 A1 discloses a bite block which is disposed on the vertically adjustable support member. The support member is designed as an eccentrically mounted roller and has two reception holes for the support member, which holes are provided for a standard radiograph and for a sinus and mandibular radiograph.

DE 102 50 005 A1 discloses a bite-block system which comprises a swivel plate mounted on a retainer. This does not allow for any height adjustment of the bite block, however, since only the angle of inclination of the chewing plane is to be considered or the X-ray device has to be adjusted to a pre-assigned value.

However, it sometimes occurs that in the predefined positions when performing transverse tomography (TSA) of the molars, the ramus, i.e. the lower edge of the mandible is not completely imaged.

Radiographs in the central part of the face, i.e. above the upper jaw are also sometimes incomplete, especially that of the mandibular joint.

WO 02/086619 A1 discloses a tomographic device for dental tomosynthesis in which the bite block is affixed to an articulated arm and said arm engages a locking bolt when the patient is in the correct position. The disadvantage here is that no standard positions can be set.

It is an object of the invention, as characterized in the claims, to provide an apparatus for the correct positioning of a patient when being radiographed with a medical panorama X-ray imaging device, permitting simple and firm positioning of a patient.

SUMMARY OF THE INVENTION

This object is achieved according to the invention by a positioning device which includes a retainer disposed in a fixed direction relative to an X-ray apparatus, and a variable positioner connected thereto, the retainer having a longitudinal guide for the positioner to enable vertical adjustment of the positioner relative to the retainer.

The advantage gained is that the operator does not have to change the positioners for different radiographs but only carries out vertical adjustment. Instead of the three bite blocks used hitherto, i.e. one standard bite element and two bite elements for the midfacial radiographs and accordingly three supporting elements, a single bite block and a single supporting element may be used. This reduces the risk of omitting to change the positioner for body size adjustment.

Advantageously, the retainer has a socket for fixation on a support of the X-ray device and the longitudinal guide is set axially at a distance from the socket, advantageously in the direction toward the patient. This makes it possible to move the positioner past the carrier during longitudinal displacement.

Advantageously, detents corresponding to a normal jaw can be provided for the positioner in the longitudinal guide for predefined standard levels. This permits rapid and secure fixation at the correct level.

In the longitudinal guide for fixation of the positioner, fixing means are advantageously provided in positions lying outside of the detents. By such means it is possible to effect individual adaptations to the anatomical peculiarities of the patient.

Advantageously, the standard levels of the positioner are coded on the positioner by marks such that incorrect settings are largely obviated.

Marks that are clearly distinguishable from each other by color are particularly suitable.

BRIEF DESCRIPTION OF THE DRAWINGS

The invention is explained with reference to an exemplary embodiment. In the drawings:

FIG. 1 shows a schematic representation of a panorama X-ray imaging device comprising a positioning device comprising a positioner in the form of a bite block or a supporting block, FIG. 2 shows a positioning device comprising a bite block, FIG. 3 shows a positioning device comprising a supporting block.

DESCRIPTION OF EMBODIMENTS

FIG. 1 is a schematic representation of a panorama X-ray imaging device 10 in which a swiveling unit 12 disposed on a column 11 carries a radiation source 13 and a detector camera 14 located opposite it. On the column 11, in addition, there is a carrier 15 comprising a holder 16 for a positioning device 17 comprising a retainer 18 for a positioner 19 that is vertically adjustable relative to the retainer 18.

Adaptation of the device 10 to the body size of the patient is accomplished by adjustment of the rotating unit 12, if necessary together with vertical adjustment of the support 15. Adaptation for the type of radiograph is accomplished by adjustment of the positioning device 17.

FIG. 2 is a perspective view of the positioning device 17 according to an exemplary embodiment of the invention comprising a bite block 19. The positioning device 17 has a retainer 18 on which the bite block 19 is guided longitudinally by means of a longitudinal guide 20. The bite block 19 also has a guided adjusting segment 19.1 and a bite plate 19.2 disposed at an angle thereto.

The longitudinal guide 20 is axially spaced from a socket 21 relative to the patient and it at least partially encircles the adjusting segment 19.1 of the bite block 19. The adjusting segment 19.1 contains detents for arresting it in the longitudinal guide 20 at predefined standard heights suitable for a normal jaw. In order to produce a definite locking position, a spring-loaded tongue on the longitudinal guide 20 can engage a groove 25, 26 in the adjusting segment. Intermediate positions are not usually required but may be provided by means of a clamping mechanism, which causes two parts on the bite block 19 to be upwardly or downwardly pushed against the retainer 18.

On the adjusting segment 19.1 there are provided three marks 22 to 24.1 as well as one mark 24.2 at different levels, to which the locking positions of the adjusting segment 19.1 in the longitudinal guide may correspond. The marks 22 to 24.2 may correspond to the different standard bite elements used hitherto for the standard radiograph, for the sinus and mandibular radiographs and for other mandibular radiographs produced from a different X-raying direction.

The top mark 22 serves for positioning the patient for creating a transversal tomograph of the midface, also called a midfacial radiograph or sinus radiograph, and of the upper jaw, also called a maxillary tomograph.

The second highest mark 23 serves for positioning the patient for making a mandibular radiograph. In addition, in this position a midfacial radiograph or sinus radiograph and a maxillary radiograph may also be taken. These radiographs are also transverse tomographs.

The second lowest mark 24.1 serves for positioning the patient for taking a standard panorama tomograph as well as other standard radiographs. In addition, in this position a transverse tomograph of the mandible can also be taken, also called a mandibular radiograph.

The bottom mark 24.2 serves for positioning the patient for taking a transverse tomograph of the mandible in an even lower position.

To prevent the risk of incorrect positioning, the marks 22 to 24.2 may be distinguished from each other by color coding.

FIG. 3 shows a subnasal support 29 for patients having no front teeth, which has an adjusting segment 29.1 that is somewhat longer than in the case of the bite block 19 shown in FIG. 2 so that a supporting segment 29.2 is higher than the bite block 19.2. The supporting piece 29 is also color coded and corresponds in its connection zone to the bite block 19 shown in FIG. 2 so that it can be inserted into the holder 20 in place of the bite block 19.

The invention claimed is:

1. A positioning device for positioning a patient in a panorama X-ray apparatus comprising a retainer disposed in a fixed direction relative to the X-ray apparatus and a variable positioner connected thereto, wherein said retainer has a longitudinal guide for the positioner to enable vertical adjustment of said positioner relative to said retainer, and including detents in said positioner to enable arrestment thereof in said longitudinal guide at predefined standard levels corresponding to a normal jaw.

2. The positioning device according to claim 1, wherein said positioner is a bite block or a support.

3. The positioning device according to claim 1 or claim 2, wherein said retainer includes a socket adapted for attachment to a carrier of said X-ray apparatus and said longitudinal guide is set at an axial distance from said socket 4. The positioning device according to claim 1, including locking means in said longitudinal guide for fixation of said positioner in positions outside of said detents.

5. The positioning device according to claim 4, wherein different standard levels are marked on said positioner by means of marks.

6. The positioning device according to claim 5, wherein said marks are clearly distinguishable from each other by color coding.

* * * * *